United States Patent [19]

Cai et al.

[11] Patent Number: 5,609,963
[45] Date of Patent: Mar. 11, 1997

[54] ANHYDRIDE-FUNCTIONAL MONOMERS AND POLYMERS AND REACTIVE COMPOSITIONS PREPARED FROM SAME

[75] Inventors: Rubing Cai; Thomas W. Yokoyama, both of Chicago, Ill.

[73] Assignee: The Sherwin-Williams Company, Cleveland, Ohio

[21] Appl. No.: 611,441

[22] Filed: Mar. 1, 1996

Related U.S. Application Data

[62] Division of Ser. No. 336,033, Nov. 8, 1994, Pat. No. 5,580,995, which is a division of Ser. No. 176,732, Jan. 3, 1994, Pat. No. 5,364,945.

[51] Int. Cl.$^6$ ........................................................ B32B 27/08
[52] U.S. Cl. ............................ 428/515; 428/413; 428/414
[58] Field of Search .................... 428/515, 413, 428/414, 4

[56] References Cited

U.S. PATENT DOCUMENTS

| | | | |
|---|---|---|---|
| 2,884,408 | 4/1959 | Phillips et al. | 260/78.3 |
| 3,523,143 | 8/1970 | Kwong | 260/835 |
| 3,975,314 | 8/1976 | Smyk et al. | 260/2 |
| 4,026,867 | 5/1977 | Gardiner | 260/46 |
| 4,107,114 | 8/1978 | Nakayama et al. | 260/22 |
| 4,374,235 | 2/1983 | Culbertson et al. | 526/262 |
| 4,417,037 | 11/1983 | Muisers et al. | 526/271 |
| 4,599,432 | 7/1986 | Kuroda et al. | 549/255 |
| 4,703,101 | 10/1987 | Singer et al. | 528/87 |
| 4,720,555 | 1/1988 | Nash | 549/252 |
| 4,859,758 | 8/1989 | Shalati et al. | 527/313 |
| 4,871,806 | 10/1989 | Shalati et al. | 525/108 |
| 4,877,887 | 10/1989 | Becker et al. | 549/253 |
| 4,927,868 | 5/1990 | Schimmel et al. | 523/439 |
| 4,946,744 | 8/1990 | Shalati et al. | 428/500 |
| 5,066,742 | 11/1991 | Gupta | 526/216 |
| 5,093,391 | 3/1992 | Barsotti et al. | 523/400 |
| 5,206,295 | 4/1993 | Harper et al. | 525/207 |
| 5,227,243 | 7/1993 | Shalati et al. | 428/457 |
| 5,243,069 | 9/1993 | Emmons | 560/224 |

FOREIGN PATENT DOCUMENTS

| | | |
|---|---|---|
| 4627530 | 8/1971 | Japan . |
| 4843191 | 12/1973 | Japan . |
| 5780408 | 5/1982 | Japan . |
| 1225964 | 9/1989 | Japan . |

OTHER PUBLICATIONS

Chemical Abstract 101: 131184q Vinyl citrates from citric acid as new monomers (Muisers et al.).
Makromol. Chem., Rapid Commun. 8, 281–284 (1987) *Copolymerization of 1–hexene–3,4–cioic anhydride and its thermal rearrangement products with styrene.*
Salit, N. I., Chemical Abstract 63:684 E–H.

*Primary Examiner*—Ralph H. Dean
*Attorney, Agent, or Firm*—Robert E. McDonald; Steven W. Tan; Heidi A. Boehlefeld

[57] ABSTRACT

Anhydride-functional polymerizable monomers having the structure:

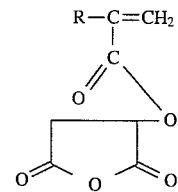

and polymers and reactive compositions prepared from these monomers are disclosed. The reactive compositions are especially useful in primer and clearcoat/basecoat applications.

37 Claims, No Drawings

ANHYDRIDE-FUNCTIONAL MONOMERS AND POLYMERS AND REACTIVE COMPOSITIONS PREPARED FROM SAME

This is a divisional of application Ser. No. 08/336,033 filed on Nov. 8, 1994, which was, in turn, a divisional of Ser. No. 08/176,732 filed on Jan. 3, 1994, (now U.S. Pat. No. 5,364,945).

BACKGROUND OF THE INVENTION

1. Field of the Invention.

This invention involves novel anhydride-functional polymerizable monomers and polymers and reactive compositions prepared from those monomers. The anhydride-functional monomers have the structure:

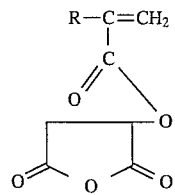

wherein R is hydrogen or methyl.

This invention also relates to anhydride-functional polymers having an average of at least two anhydride groups per molecule and which are obtained by polymerizing, under free radical addition polymerization conditions, (i) the anhydride-functional monomer of this invention; and (ii) optionally, at least one other unsaturated monomer copolymerizable with the anhydride-functional monomer.

This invention also relates to novel reactive compositions which utilize the anhydride-functional polymer. The polymers are useful as corrosion or scale inhibitors, thickeners, dispersants and as reactive agents and/or crosslinking agents for compounds having functional groups, such as epoxy, hydroxyl or amine groups, which are reactive with anhydride groups. The anhydride-functional polymers can, therefore, be utilized in a variety of materials such as plastics, fibers, adhesives, paper sizing, inks and, particularly, coating compositions. The reactive compositions can be reacted at room temperature or force dried at temperatures ranging up to about 350° F. or higher if desired. When utilized as reactive crosslinking agents for coatings, the anhydride-functional polymers may be utilized in a variety of coating applications, including primers and topcoats as well as clearcoats and/or basecoats in clearcoat/basecoat compositions. The monomers themselves can be utilized as crosslinkers, neutralizers, scale preventatives, thickeners and many other applications.

The coatings typically involve the combination of the anhydride-functional polymer with materials reactive with anhydrides such as polyepoxides, polyamines, polyols, etc. One preferred curable coating combination comprises the anhydride-functional polymer and a polyol, preferably a hydroxy-functional polymer, optionally in combination with an epoxide or polyepoxide. Another preferred curable coating combination comprises the anhydride-functional polymer, an acid-functional compound, an epoxide or polyepoxide, and, optionally, a polyol. All of these combinations provide fast reacting, durable coatings which minimize the toxicity problems which may be associated with other low temperature curing systems.

2. Description of the Prior Art.

Unsaturated anhydrides, such as maleic anhydride, and copolymers made from maleic anhydride are known in the art. Such anhydride copolymers are heterogeneous with respect to the distribution of anhydride groups along the backbone of the polymer due to the abnormal copolymerization behavior of maleic anhydride with other monomers, and the acid groups generated from opening these anhydrides by reaction with hydroxyl or amine groups are not highly reactive for further cure reactions, e.g. with epoxy groups, due to steric hindrance arising from the proximity of the anhydride ring to the polymer backbone. Such anhydride-functional polymers are also relatively viscous and are difficult to utilize in combination with low levels of solvent. Additionally, such polymers may form dark colored materials when certain base catalysts, such as N-methyl imidazole, are used to accelerate a subsequent reaction of the polyanhydride with reactive materials such as hydroxy-functional compounds.

Coating compositions comprising polyanhydrides and hydroxy-functional compounds are known in the art. For example, U.S. Pat. No. 4,946,744 teaches clearcoat/basecoat combinations involving (i) a polyanhydride, for example, such as that prepared by copolymerization of maleic anhydride with (meth)acrylic monomers, and (ii) a polyol. U.S. Pat. No. 4,871,806 teaches curable compositions comprising a polyanhydride, a polyacid, a polyol and an epoxy-functional compound. U.S. Pat. No. 4,374,235 teaches anhydride-functional polymers prepared by the polymerization of an alkenyl succinic anhydride and a vinyl monomer. The prior art has not, however, taught polymers obtained by the polymerization of the novel anhydride monomers of this invention.

BRIEF SUMMARY OF THE INVENTION

This invention involves polymerizable unsaturated monomers having pendent anhydride functionality. These versatile monomers have a variety of potential applications due to their combination of reactive sites. Either the anhydride or the unsaturation functionality could be reacted first, followed, if desired, by subsequent reaction of the other functionality. For example, the anhydride group could be reacted with hydroxyl groups on an alcohol or polyol to provide a product having one or more pendent, polymerizable unsaturation sites. Such a product could be subsequently polymerized, either with or without additional copolymerizable monomers such as styrene or (meth)acrylic monomers, by peroxide initiation or by exposure to high energy radiation such as electron beam or ultraviolet light. The anhydride-functional monomer could also be hydrolyzed to produce a diacid-functional monomer.

A particularly preferred use for the monomers of this invention involves their use in polymers derived by polymerizing the anhydride monomer through its unsaturation either as a homopolymer or, preferably, in combination with one or more additional copolymerizable monomers. The anhydride-functional polymers can be, if desired, fully or partially hydrolyzed, or ring opened by e.g. half-ester or half-amide reactions, to produce acid-functional polymers, or they can be directly utilized as crosslinking agents for materials having an average of at least two functional groups per molecule which are reactive with anhydride groups, such as epoxy, hydroxyl or amine functionality.

Therefore, this invention also relates to curable compositions which comprise (i) anhydride-functional polymers prepared using the monomers of this invention, and (ii) a compound having an average of at least two functional groups per molecule which are reactive with anhydride groups. A particularly preferred curable composition comprises (i) the anhydride-functional polymer and (ii) a hydroxy-functional compound having an average of at least two hydroxyl groups per molecule, optionally in combination with an epoxide or polyepoxide. Another preferred combination comprises (i) the anhydride-functional polymer, (ii) an acid-functional compound having an average of at least two acid groups per molecule, (iii) an epoxide or polyepoxide, and, optionally, (iv) a hydroxy-functional compound having an average of at least two hydroxyl groups per molecule. Another useful composition comprises (i) the anhydride-functional polymer and (ii) a polyamine compound having an average of at least two primary and/or secondary amine groups per molecule. The term "compound" is used in its broadest sense to include monomers, oligomers and polymers.

Although the curable compositions of this invention can be utilized without solvent in many applications, it is frequently preferred to utilize them in combination with about 5 to about 50% by weight of an inert solvent. It is convenient to provide the curable composition as a multicomponent system which is reactive upon mixing the components. Especially preferred is a two-component system wherein the anhydride-functional polymer and the acid-functional compound, if utilized, are combined in one package and the epoxy-functional compound and/or the hydroxy-functional compound provide a second package. The two packages can then be mixed together to provide the curable composition immediately prior to use.

In one preferred application, this invention also relates to coated substrates having a multi-layer decorative and/or protective coating which comprises:

(a) a basecoat comprising a pigmented film-forming polymer; and (b) a transparent clearcoat comprising a film-forming polymer applied to the surface of the basecoat composition; wherein the clearcoat and/or the basecoat comprises the curable compositions of this invention. The term "film forming polymer" means any polymeric material that dan form a film from evaporation of any carrier or solvent.

Accordingly, one object of this invention is to provide novel unsaturated anhydride-functional monomers and polymers therefrom. Another object is to provide improved curable compositions having excellent reactivity at low temperatures. It is a further object of this invention to provide coating compositions which may be utilized as primers, topcoats or clearcoats and/or basecoats in clearcoat/basecoat compositions. Another object of this invention is to provide an improved two-package coating composition wherein one package comprises a novel anhydride-functional polymer and, optionally, an acid-functional compound and the other package comprises an epoxy-functional compound and/or a hydroxy-functional compound. Another object of this invention is to provide coatings having excellent reactivity, durability and corrosion resistance. A further object of this invention is to provide improved coating compositions which can be cured at room temperature or force dried at elevated temperatures. It is also an object of this invention to provide curable compositions which are relatively low in viscosity and which can be utilized with reduced amounts of volatile organic solvents. These and other objects of the invention will become apparent from the following discussions.

DETAILED DESCRIPTION OF THE INVENTION

The unsaturated anhydride monomers of this invention can be conveniently prepared by the reaction of (i) an unsaturated acid derivative having the structure:

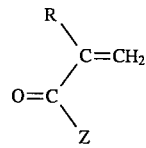

wherein Z is Cl, Br or

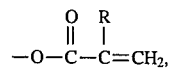

and each R is individually H or methyl, with (ii) malic acid at temperatures ranging up to about 140° C., preferably from about 70° C. to about 95° C. Representative examples of the unsaturated acid derivative are acrylic anhydride, methacrylic anhydride, acryloyl bromide, methacryloyl bromide, acryloyl chloride and methacryloyl chloride. Due to cost, reactivity and the generation of fewer byproducts, methacrylic anhydride is especially preferred as the unsaturated acid derivative. It is useful to include a polymerization inhibitor, such as butylated hydroxytoluene, t-butyl catechol, phenol hydroquinone, quinone, etc., in the reaction mixture to prevent the polymerization of the acrylic or methacrylic double bonds during the manufacture of the monomer. Commercially available samples of the acrylic or methacrylic anhydride normally already contain a small amount of inhibitor and additional inhibitors may not be necessary.

The reaction to produce the unsaturated anhydride monomer can be conducted as a multi-step synthesis. In the first step, 0.9 to about 1.2, and especially 1.0 to about 1.1, moles of the unsaturated acid derivative are reacted with about 1.0 moles of malic acid at temperatures ranging up to about 140° C., and preferably about 70° C to about 95° C. normally in the presence of an inert solvent such as methyl ethyl ketone, methyl amyl ketone, etc. The initial reaction of the unsaturated acid derivative is primarily with the hydroxyl group of the malic acid to produce the (meth)acryloxy succinic acid. This dicarboxylic acid can subsequently be cyclized to produce the (meth)acryloxy succinic anhydride derivative in several ways. If desired, the dicarboxylic acid can be thermally cyclized by heating the dicarboxylic acid at temperatures of at least about 100° C., and typically ranging between about 120° C. to about 140° C. Alternatively, the dicarboxylic acid can be reacted with at least an equimolar amount of a reactant which will produce a better leaving group than the carboxylic acid —OH. For example, the dicarboxylic acid can be reacted with acetic anhydride followed by subsequent displacement of acetic acid upon ring closure. The reaction of the acetic anhydride and the dicarboxylic acid (typically 1 to 5 moles of acetic anhydride would be provided for each mole of diacid) can typically be conducted at temperatures ranging from about 60° C. to about 120° C., preferably 80° C. to 100° C., for approximately 1 to 2 hours. The reaction is representatively shown below wherein the unsaturated acid derivative is methacrylic anhydride and the methacryloxy succinic acid product is subsequently cyclized to produce the methacryloxy succinic anhydride derivative by either thermal cyclization or by reaction with acetic anhydride and subsequent ring closure:

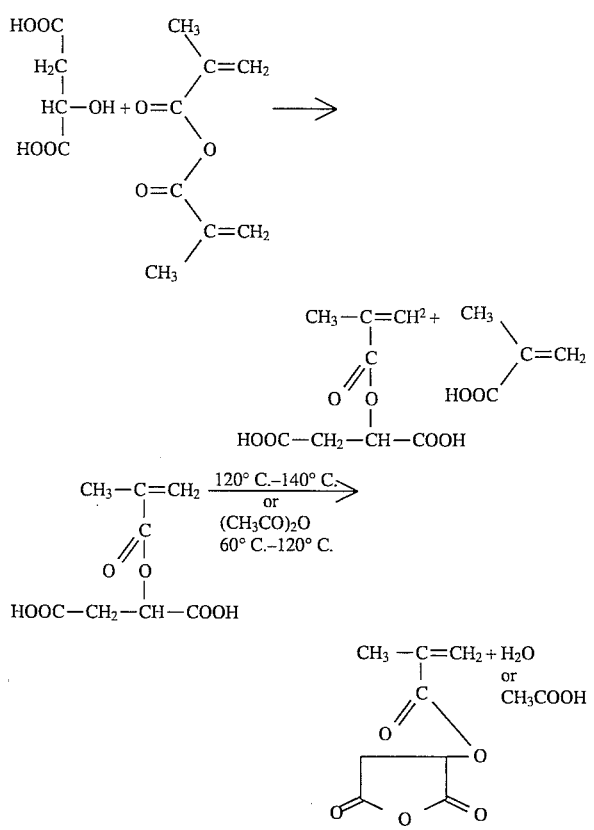

The monomer producing reaction can also be conducted as a single-step synthesis resulting in the addition of the unsaturation and the ring closure to produce the anhydride ring. The reaction is representatively shown below wherein the unsaturated acid derivative which is reacted with the malic acid is methacrylic anhydride:

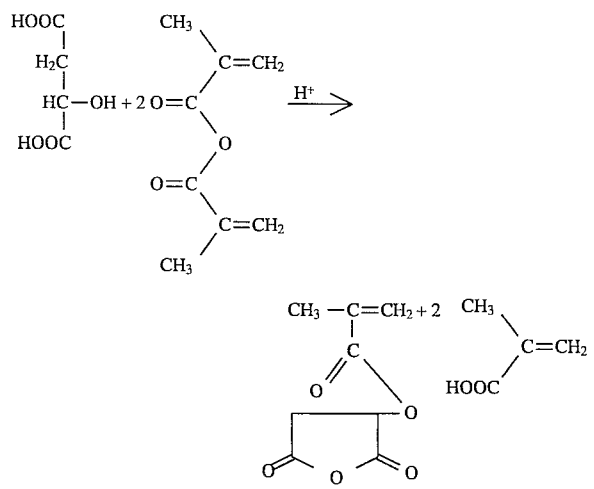

Typically, the unsaturated acid derivative and the malic acid, which can be either an optically active form or the racemic form of the acid, will be reacted, optionally in the presence of an inert solvent such as a ketone, at temperatures of 25° C. to about 140° C., preferably about 70° C. to 95° C., for about 10 minutes to two hours. When acrylic anhydride or methacrylic anhydride is utilized as the unsaturated acid derivative, the reaction is normally conducted in the presence of an acid catalyst, typically in the range of 0.01 to about 0.2 percent by weight of the total amount of malic acid and unsaturated acid derivative. When the single-step synthesis is utilized, the reactants are mixed to provide a ratio of moles of unsaturated acid derivative to moles of malic acid of from about 1.9:1.0 to about 4.0:1.0. It is especially preferred to use a ratio of moles of unsaturated acid derivative to moles of malic acid between 2.0:1.0 to about 3.0:1.0.

Although, it is not our intent to be bound by theory, it is believed that in the single-step synthesis, the unsaturated acid derivative reacts with the OH substituent and also with one of the carbonyl groups of the diacid to effect ring closure. Therefore, theoretically a 2:1 mole ratio of the unsaturated acid derivative to malic acid is optimum for the single-step synthesis. One of the unique advantages of this one-step process is that both the cyclization to produce the succinic anhydride ring and the introduction of the acrylic or methacrylic unsaturation adjacent to the succinic anhydride ring is effected by the same reactant so that difficult separation and purification of intermediate products is avoided. Additionally, when the unsaturated acid derivative is acrylic anhydride or methacrylic anhydride, the acrylic acid or methacrylic acid by-product of the monomer-producing reaction can be recovered by distillation from the final product mixture and, if desired, utilized in other applications.

Methacrylic anhydride, which is commercially available from Rohm Tech, Inc. of Malden, Mass., and acrylic anhydride, which is commercially available from Polysciences, Inc. of Warrington, Penn., are especially preferred in the practice of this invention. The acryloyl chloride and methacryloyl chloride can be conveniently prepared by the reaction of the corresponding acid and a chlorinating agent such as thionyl chloride, as is well known in the art. The bromide materials can be prepared in a similar fashion using brominating agents. The polymerization of the novel monomers of this invention either alone or with other unsaturated copolymerizable monomers, such as (meth)acrylic or styrene monomers, proceeds at excellent yield and provides polymers having excellent reactivity, flexibility and overall performance. The reactivity and flexibility are due, at least in part, to the fact that the anhydride groups are separated by at least several atoms from the backbone of the polymer.

1. ANHYDRIDE-FUNCTIONAL POLYMERS

The anhydride-functional polymers which are useful in the practice of this invention will have an average of at least two anhydride groups per molecule and are prepared by polymerizing the anhydride monomers and normally at least one other copolymerizable monomer under free radical addition polymerization conditions. The monomers which are copolymerized with the anhydride monomer should be free of any functionality which could react with the anhydride group during the polymerization. The anhydride-functional polymers can be conveniently prepared by conventional free radical addition polymerization techniques. Typically the polymerization will be conducted in an inert solvent and in the presence of an initiator, such as a peroxide or azo compound, at temperatures ranging from 35° C. to about 200° C., and especially 75° C. to about 150° C. Representative initiators include di-t-butyl peroxide, di-t-amyl peroxide, cumene hydroperoxide, t-butyl peroctoate, azobis(isobutyronitrile) and ethyl 3,3-di(t-amylperoxy)-butyrate.

The anhydride-functional monomers should generally comprise about 5% to 100%, by weight of the monomer mixture used to prepare the anhydride-functional polymer. The remaining 0 to 95% by weight of the monomer mixture, will comprise other reactants copolymerizable with the anhydride-functional monomer. An especially preferred anhydride-functional free radical addition polymer comprises the free radical polymerization product of (a) 5 to 60, and especially 15 to about 40, weight percent of the anhydride monomer; and (b) 40 to 95, and especially 60 to about 85, weight percent of at least one other unsaturated monomer copolymerizable with the anhydride monomer.

Representative useful copolymerizable (meth)acrylic monomers include methyl acrylate, ethyl acrylate, propyl acrylate, isopropyl acrylate, butyl acrylate, isobutyl acrylate, ethyl hexyl acrylate, amyl acrylate, 3,5,5-trimethylhexyl acrylate, methyl methacrylate, ethyl methacrylate, propyl methacrylate, isobornyl methacrylate, lauryl methacrylate, acrylic acid, methacrylic acid, acrylonitrile, methacrylonitrile, acrylamide and methacrylamide.

Other monomers which are free of (meth)acrylic functionality which could also be used in the polymers of this invention include vinyl acetate, vinyl propionate, vinyl butyrate, vinyl isobutyrate, vinyl benzoate, vinyl m-chlorobenzoate, vinyl p-methoxy benzoate, vinyl chloride, styrene, alpha-methyl styrene, maleic anhydride, etc.

2. ACID-FUNCTIONAL COMPOUNDS

The acid-functional compounds which, optionally, can be used in combination with the anhydride-functional polymers of this invention in preparing curable compositions should have an average of at least two carboxylic acid groups per molecule. Although low molecular weight diacids and polyacids such as phthalic acid, succinic acid, adipic acid, azelaic acid, maleic acid, fumaric acid, trimellitic acid and trimesic acid can be utilized in combination with the anhydride-functional polymers in the practice of this invention, it is especially preferred to utilize polymeric acid-functional compounds.

Preferably the acid-functional polymer will have a number average molecular weight of at least about 400. Typical number average molecular weights of the carboxylic acid-functional polymers will range from about 500 to about 30,000. Representative acid-functional polymers include acrylics, polyesters and polymers prepared by the reaction of anhydrides with hydroxy-functional polymers as discussed more fully below.

2.A. Carboxylic acid-functional polymers prepared by the half-ester forming reaction of anhydrides and hydroxy-functional polymers.

Especially preferred as acid-functional compounds in the curable compositions of this invention are the carboxylic acid-functional polymers prepared by the half-ester opening of the cyclic anhydride by reaction with a hydroxyl group on the hydroxy-functional polymer to form one ester group and one acid group.

Typically, the hydroxy-functional polymers will have number average molecular weights of at least about 400 and typical number average molecular weights will range from about 400 to about 30,000, and especially 1,000 to about 15,000. Methods of preparing hydroxy-functional polymers are well known in the art and the method of preparation of the hydroxy-functional molecule or polymer which is reacted with the cyclic carboxylic anhydride to produce the optional acid-functional polymer is not critical to the practice of this invention. Representative polymers which can be reacted with arthydrides to produce the acid-functional polymers include the hydroxy-functional polyethers, polyesters, acrylics, polyurethanes, polycaprolactones, etc. as generally discussed in Sections 2.A. 1. through 2.A.5. below.

2.A. 1.

Polyether polyols are well known in the art and are conveniently prepared by the reaction of a diol or polyol with the corresponding alkylene oxide. These materials are commercially available and may be prepared by a known process such as, for example, the processes described in *Encyclopedia of Chemical Technology*, Volume 7, pages 257–262, published by Interscience Publishers, Inc., 1951; and in Kirk-Othmer *Encyclopedia of Chemical Technology*, Volume 18, pages 638–641, published by Wiley-International, 1982. Representative examples include the polypropylene ether glycols and polyethylene ether glycols such as those marketed as Niax® Polyols from Union Carbide Corporation.

2.A.2.

Another useful class of hydroxy-functional polymers are those prepared by condensation polymerization reaction techniques as are well known in the art. Representative condensation polymerization reactions include polyesters prepared by the condensation of polyhydric alcohols and polycarboxylic acids or anhydrides, with or without the inclusion of drying oil, semi-drying oil, or non-drying oil fatty acids. By adjusting the stoichiometry of the alcohols and the acids while maintaining an excess of hydroxyl groups, hydroxy-functional polyesters can be readily produced to provide a wide range of desired molecular weights and performance characteristics.

The polyester polyols are derived from one or more aromatic and/or aliphatic polycarboxylic acids, the anhydrides thereof, and one or more aliphatic and/or aromatic polyols. The carboxylic acids include the saturated and unsaturated polycarboxylic acids and the derivatives thereof, such as maleic acid, fumaric acid, succinic acid, adipic acid, azelaic acid, and dicyclopentadiene dicarboxylic acid. The carboxylic acids also include the aromatic polycarboxylic acids, such as phthalic acid, isophthalic acid, terephthalic acid, etc. Anhydrides such as maleic anhydride, phthalic anhydride, trimellitic anhydride, or Nadic Methyl Anhydride (brand name for methylbicyclo[2.2.1]heptene-2,3-dicarboxylic anhydride isomers) can also be used.

Representative saturated and unsaturated polyols which can be reacted in stoichiometric excess with the carboxylic acids to produce hydroxy-functional polyesters include diols such as ethylene glycol, dipropylene glycol, 2,2,4-trimethyl 1,3-pentanediol, neopentyl glycol, 1,2-propanediol, 1,3-propanediol, 1,4-butanediol, 1,3-butanediol, 2,3-butanediol, 1,5-pentanediol, 1,6-hexanediol, 2,2-dimethyl-1,3-propanediol, 1,4-cyclohexanedimethanol, 1,2-cyclohexanedimethanol, 1,3-cyclohexanedimethanol, 1,4-bis(2-hydroxyethoxy)cyclohexane, trimethylene glycol, tetra methylene glycol, penta-methylene glycol, hexamethylene glycol, decamethylene glycol, diethylene glycol, triethylene glycol, tetraethylene glycol, norbornylene glycol, 1,4-benzenedimethanol, 1,4-benzenediethanol, 2,4-dimethyl-2-ethylenehexane- 1,3-diol, 2-butene- 1,4-diol, and polyols such as trimethylolethane, trimethylolpropane, trimethylolhexane, triethylolpropane, 1,2,4-butanetriol, glycerol, pentaerythritol, dipentaerythritol, etc.

Typically, the reaction between the polyols and the polycarboxylic acids is conducted at about 120° C. to about 200° C. in the presence of an esterification catalyst such as dibutyl tin oxide.

2.A.3.

Additionally, hydroxy-functional polymers can be prepared by the ring opening reaction of epoxides and/or polyepoxides with primary or, preferably, secondary amines or polyamines to produce hydroxy-functional polymers. Representative amines and polyamines include ethanol amine, N-methylethanol amine, dimethyl amine, ethylene diamine, isophorone diamine, etc. Representative polyepoxides include those prepared by condensing a polyhydric alcohol or polyhydric phenol with an epihalohydrin, such as epichlorohydrin, usually under alkaline conditions. Some of these condensation products are available commercially under the designations EPON or DRH from Shell Chemical Company, and methods of preparation are representatively taught in U.S. Pat. Nos. 2,592,560; 2,582,985 and 2,694,694.

2.A.4.

Other useful hydroxy-functional polymers can be prepared by the reaction of an excess of at least one polyol, such as those representatively described in Section 2.A.2 above, with polyisocyanates to produce hydroxy-functional urethanes. Representative polyisocyanates having two or more isocyanate groups per molecule include the aliphatic compounds such as ethylene, trimethylene, tetramethylene, pentamethylene, hexamethylene, 1,2-propylene, 1,2-butylene, 2,3-butylene, 1,3-butylene, ethylidene and butylidene diisocyanates; the cycloalkylene compounds such as 3-isocyanatomethyl-3,5,5 -trimethylcyclohexylisocyanat, and the 1,3-cyclopentane, 1,3-cyclohexane, and 1,2-cyclohexane diisocyanates; the aromatic compounds such as m-phenylene, p-phenylene, 4,4'-diphenyl, 1,5-naphthalene and 1,4-naphthalene diisocyanates; the aliphatic-aromatic compounds such as 4,4'-diphenylene methane, 2,4- or 2,6- toluene, or mixtures thereof, 4,4'-toluidine, and 1,4-xylylene diisocyanates; the nuclear substituted aromatic compounds such as dianisidine diisocyanate, 4,4'-diphenylether diisocyanate and chlorodiphenylene diisocyanate; the triisocyanates such as triphenyl methane-4,4', 4"-triisocyanate, 1,3,5-triisocyanate benzene and 2,4,6-triisocyanate toluene; and the tetraisocyanates such as 4,4'-diphenyl-dimethyl methane-2,2'-5,5'-tetraisocyanate; the polymerized polyisocyanates such as tolylene diisocyanate dimers and trimers, and other various polyisocyanates containing biuret, urethane, and/or allophanate linkages. The polyisocyanates and the polyols are typically reacted at temperatures of 25° C. to about 150° C. to form the hydroxy-functional polymers.

2.A.5.

Useful hydroxy-functional polymers can also be conveniently prepared by free radical polymerization techniques such as in the production of acrylic resins. The polymers are typically prepared by the addition polymerization of one or more monomers. At least one of the monomers will contain, or can be reacted to produce, a reactive hydroxyl group. Representative hydroxy-functional monomers include 2-hydroxyethyl acrylate, 2-hydroxyethyl methacrylate, 2-hydroxypropyl acrylate, 4-hydroxybutyl methacrylate, 2-hydroxypropyl methacrylate, 3-hydroxybutyl acrylate, 4-hydroxybutyl acrylate, 4-hydroxypentyl acrylate, 2-hydroxyethyl ethacrylate, 3-hydroxybutyl methacrylate, 2-hydroxyethyl chloroacrylate, diethylene glycol methacrylate, tetra ethylene glycol acrylate, para-vinyl benzyl alcohol, etc. Typically the hydroxy-functional monomers would be copolymerized with one or more monomers having ethylenic unsaturation such as:

(i) esters of acrylic, methacrylic, crotonic, tiglic, or other unsaturated acids such as: methyl acrylate, ethyl acrylate, propyl acrylate, isopropyl acrylate, butyl acrylate, isobutyl acrylate, ethylhexyl acrylate, amyl acrylate, 3,5,5-trimethylhexyl acrylate, methyl methacrylate, ethyl methacrylate, propyl methacrylate, dimethylaminoethyl methacrylate, isobornyl methacrylate, t-butyl methacrylate, ethyl tiglate, methyl crotonate, ethyl crotonate, etc.;

(ii) vinyl compounds such as vinyl acetate, vinyl propionate, vinyl butyrate, vinyl isobutyrate, vinyl benzoate, vinyl m-chlorobenzoate, vinyl p-methoxybenzoate, vinyl alpha-chloroacetate, vinyl toluene, vinyl chloride, etc.;

(iii) styrene-based materials such as styrene, s-methyl styrene, α-ethyl styrene, α-bromo styrene, 2,6-dichlorostyrene, etc.;

(iv) allyl compounds such as allyl chloride, allyl acetate, allyl benzoate, allyl methacrylate, etc.;

(v) other copolymerizable unsaturated monomers such as ethylene, acrylonitrile, methacrylonitrile, dimethyl maleate, isopropenyl acetate, isopropenyl isobutyrate, acrylamide, methacrylamide, and dienes such as 1,3-butadiene, etc. The polymers are conveniently prepared by conventional free radical addition polymerization techniques. Frequently, the polymerization will be catalyzed by conventional initiators known in the art to generate a free radical such as t-butyl peroxyoctoate, t-butyl peroxybenzoate, di-t-butyl peroxide, di-t-amyl peroxide, azobis-(isobutyronitrile), cumene hydroperoxide, t-butyl perbenzoate, etc. Typically, the acrylic monomers are heated in the presence of the catalyst at temperatures ranging from about 35° C. to about 200° C., and especially 75° C. to 150° C., to effect the polymerization. The molecular weight of the polymer can be controlled, if desired, by the monomer selection, reaction temperature and time, and/or the use of chain transfer agents as is well known in the art.

Especially preferred polymers in the practice of this invention for reaction with the cyclic anhydride to produce the carboxylic acid-functional polymers are hydroxy-functional polyesters and hydroxy-functional acrylic polymers. An especially preferred hydroxy-functional polymer is the addition polymerization reaction product of (a) 5 to 100, and especially 10 to about 40, weight percent of a hydroxy-functional ethylenically unsaturated monomer and (b) 0 to 95, and especially 60 to about 90, weight percent of at least one other ethylenically unsaturated monomer copolymerizable with the hydroxy-functional monomer.

The cyclic carboxylic acid anhydrides useful in the practice of this invention to produce the carboxylic acid-functional half- ester product by reaction with the hydroxy-functional compound can be any monomeric aliphatic or aromatic cyclic anhydride having one anhydride group per molecule. Representative arthydrides include phthalic anhydride, 3-nitrophthalic anhydride, 4-nitrophthalic anhydride, 3-flourophthalic anhydride, 4-chlorophthalic anhydride, tetrachlorophthalic anhydride, tetrabromophthalic anhydride, tetrahydrophthalic anhydride, hexahydrophthalic anhydride, methylhexahydrophthalic anhydride, succinic anhydride, dodecenylsuccinic anhydride, octylsuccinic anhydride, maleic anhydride, dichloromaleic anhydride, glutaric anhydride, adipic anhydride, chlorendic anhydride, iraconic anhydride, citraconic anhydride, endo-methylenetetrahydrophthalic anhydride, cyclohexane-1,2-dicarboxylic anhydride, 4-cyclohexene-1,2dicarboxylic anhydride, 4-methyl-4-cyclohexene-1,2-dicarboxylic anhydride, 5-norbornene-2,3-dicarboxylic anhydride, 1,4-cyclohexadiene-1,2-dicarboxylic anhydride, 1,3-cyclopentanedicarboxylic anhydride, diglycolic acid anhydride, etc. Maleic anhydride is especially preferred because of its reactivity and relatively low cost. Other useful arthydrides include those anhydrides having a free carboxyl group in addition to the anhydride group such as trimellitic anhydride, aconitic anhydride, 2,6,7-naphthalene tricarboxylic anhydride, 1,2,4-butane tricarboxylic anhydride, 1,3,4-cyclopentane tricarboxylic anhydride, etc.

The reaction of the hydroxy-functional compound and the cyclic anhydride can be conducted at temperatures ranging up to about 150° C. but should normally be conducted at temperatures less than about 75° C., preferably less than 65° C., and most preferably between about 35° C. to 60° C. The reaction temperature is maintained until the reaction has proceeded to provide the desired amount of half-ester groups on the acid-functional compound. Normally, as a convenient measure of the extent of the reaction, the reaction will be continued until no change in the amount of residual unreacted anhydride can be observed, and will generally involve reacting at least about 70%, and preferably at least 95%, of the available anhydride. If the subsequent end use of the acid-functional polymer can tolerate the remaining free anhydride, if any, no separation or removal of the excess unreacted anhydride is necessary. If the end use of the acid-functional polymer requires that it be free of any unreacted anhydride, the reaction can be continued until substantially all of the anhydride has reacted, or the free anhydride may be removed by vacuum distillation or other techniques well known in the art.

The level of anhydride reacted with the hydroxy-functional compound need only be sufficient to provide the final desired acid value of the acid-functional compound. Typically the reaction would be conducted by admixing the polyol and the anhydride at levels to provide at least about 0.3 and normally about 0.7 to 1.0 anhydride groups for each hydroxyl group. By conducting the reaction at temperatures less than about 75° C. the carboxylic acid groups formed as part of the half-ester are not appreciably reactive with the hydroxyl groups themselves and so they do not compete with the ring opening half-ester reaction of the remaining arthydrides.

In order to conduct the reaction at these relatively low temperatures, it is preferred to utilize an esterification catalyst. The catalyst should be present in sufficient amount to catalyze the reaction and typically will be present at a level of at least about 0.01%, and normally from about 0.05 % to about 3.0%, based upon the weight of the cyclic anhydride. Catalysts which are useful in the esterification reaction of the anhydride with the hydroxy-functional molecule include mineral acids such as hydrochloric acid and sulfuric acid; alkali metal hydroxides such as sodium hydroxide; tin compounds such as stannous octoate, or dibutyltin oxide; aliphatic or aromatic amines, especially tertiary alkyl amines, such as triethylamine; and aromatic heterocyclic amines such as N-methyl imidazole and the like. Especially preferred are N-methyl imidazole and triethylamine.

Although the reaction between the hydroxy-functional compound and the anhydride can be conducted in the absence of solvent if the materials are liquid at the reaction temperature, it is normally preferred to conduct the reaction in the presence of an inert solvent such as esters, ketones, ethers or aromatic hydrocarbons. If desired, the acid-functional molecule can be utilized as the solvent solution, or, optionally, all or part of the inert solvent may be removed, e.g. by distillation, after the reaction is completed.

After the reaction is completed, it is frequently desirable to add a low molecular weight alcohol solvent, such as isobutanol or isopropanol, to the acid-functional compound at a level of about 5 to 35 percent by weight to provide stabilization on storage.

2.B. Carboxylic Acid-Functional Polymers Prepared From Unsaturated Acid-Functional Monomers.

Useful acid-functional polymers can also be conveniently prepared by the free radical addition polymerization of unsaturated acids such as maleic acid, acrylic acid, methacrylic acid, crotonic acid, etc. along with one or more unsaturated monomers. Representative monomers include the esters of unsaturated acids, vinyl compounds, styrene-based materials, allyl compounds and other copolymerizable monomers as representatively taught in Section 2.A.5. of this specification. The monomers which are co-polymerized with the unsaturated acid should be free of any functionality which could react with the acid groups during the polymerization.

2.C. Carboxylic Acid-Functional Polymers Prepared From Polyols and Polyacids.

Other useful acid-functional polymers include polyester polymers obtained from the reaction of one or more aromatic and/or aliphatic carboxylic acids or their arthydrides and one or more aliphatic and/or aromatic polyols wherein the acid functionality is present in a stoichiometric excess over the hydroxy functionality. Representative carboxylic acids and polyols include those listed in Section 2.A.2. of this specification.

3. EPOXY-FUNCTIONAL COMPOUNDS

The curable coatings of this invention may also incorporate at least one epoxy-functional compound. The epoxy compounds can, if there are sufficient other reactive materials to provide crosslinking, be monoepoxies or, preferably, a polyepoxide having an average of at least two epoxy groups per molecule.

Representative useful monoepoxides include the monoglycidyl ethers of aliphatic or aromatic alcohols such as butyl glycidyl ether, octyl glycidyl ether, nonyl glycidyl ether, decyl glycidyl ether, dodecyl glycidyl ether, p-tert-butylphenyl glycidyl ether, and o-cresyl glycidyl ether. Monoepoxy esters such as the glycidyl ester of versatic acid (commercially available as CARDURA® E from Shell Chemical Company), or the glycidyl esters of other acids such as tertiary-nonanoic acid, tertiary-decanoic acid, tertiary-undecanoic acid, etc. are also useful. Similarly, if desired, unsaturated monoepoxy esters such as glycidyl acrylate, glycidyl methacrylate or glycidyl laurate could be used. Additionally, monoepoxidized oils can also be used.

Other useful monoepoxies include aryl epoxides such as styrene oxide, and alkene oxides such as cyclohexene oxide, 1,2-butene oxide, 2,3-butene oxide, 1,2-pentene oxide, 1,2-heptene oxide, 1,2-octene oxide, 1,2-nonene oxide, 1,2-decene oxide, and the like.

It is only necessary that the monoepoxide compounds have a sufficiently low volatility to remain in the coating composition under the applicable conditions of cure.

Polyepoxides are especially preferred in the reactive coatings of this invention. Especially preferred as the polyfunctional epoxy compounds, due to their reactivity and durability, are the polyepoxy-functional cycloaliphatic epoxies. Preferably, the cycloaliphatic epoxies will have a number average molecular weight less than about 2,000 to minimize the viscosity. The cycloaliphatic epoxies are conveniently prepared by methods well known in the art such as epoxidation of dienes or polyenes, or the epoxidation of unsaturated esters by reaction with a peracid such as peracetic and/or performic acid.

Commercial examples of representative preferred cycloaliphatic epoxies include 3,4-epoxycyclohexylmethyl 3,4-epoxycyclohexane carboxylate (e.g. "ERL-4221" from Union Carbide Corp.); bis(3,4-epoxycyclohexylmethyl)adipate (e.g. "ERL-4299" from Union Carbide Corporation); 3,4-epoxy-6-methylcyclohexylmethyl 3,4-epoxy-6-methylcyclohexane carboxylate (e.g. "ERL-4201" from Union Carbide Corp.); bis(3,4-epoxy-6-methylcyclohexylmethyl)adipate (e.g. "ERL-4289" from Union Carbide Corp.); bis(2, 3-epoxycyclopentyl) ether (e.g. "ERL-0400" from Union Carbide Corp.); dipentene dioxide (e.g. "ERL-4269" from Union Carbide Corp.); 2-(3,4-epoxycyclohexyl-5,5-spiro-3, 4-epoxy) cyclohexanemetadioxane (e.g. "ERL-4234" from Union Carbide Corp.). Other commercially available cycloaliphatic epoxies are available from Cibh-Geigy Corporation such as CY 192, a cycloaliphatic diglycidyl ester epoxy resin having an epoxy equivalent weight of about 154. The manufacture of representative cycloaliphatic epoxies is taught in various patents including U.S. Pat. Nos. 2,884,408, 3,027,357 and 3,247,144.

Other polyepoxides potentially useful in the practices of this invention include aliphatic and aromatic polyepoxies, such as those prepared by the reaction of an aliphatic polyol or poly hydric phenol and an epihalohydrin. Other useful epoxies include epoxidized oils and epoxyfunctional copolymers such as acrylic polymers derived from ethylenically unsaturated epoxy-functional monomers such as glycidyl acrylate or glycidyl methacrylate in combination with other copolymerizable monomers such as those listed in 2.A.5 above.

4. HYDROXY-FUNCTIONAL COMPOUNDS

The hydroxy-functional compounds which are useful in combination with the anhydride-functional polymers to prepare curable compositions in the practice of this invention should have an average of at least two hydroxyl groups per molecule. Although low molecular weight diols and polyols such as propylene glycol, 1,6 hexanediol, triethanol amine and pentaerythritol can be utilized in the practice of this invention, it is especially preferred to utilize polymeric hydroxy-functional compounds such as polyethers, polyesters, acrylics, polyurethanes, polycaprolactones, etc.

Preferably the hydroxy-functional polymer will have a number average molecular weight of at least about 400. Typical number average molecular weights will range from about 400 to about 30,000, and especially 1,000 to about 15,000. In order to provide the fastest rate of reaction during cure iris preferred in the practice of this invention to utilize hydroxy-functional compounds having predominantly, and preferably all, primary hydroxy functionality.

Representative hydroxy-functional polymers are taught in Sections 2.A.1. through 2.A.5. Especially preferred as the hydroxy-functional polymer is a hydroxy-functional polymer comprising the addition polymerization reaction product of (a) 10 to about 60 weight percent of a hydroxy-functional ethylenically unsaturated monomer and (b) 40 to about 90 weight percent of at least one ethylenically unsaturated monomer copolymerizable with the hydroxy-functional monomer.

5. AMINE-FUNCTIONAL COMPOUNDS

Amine-functional compounds which are useful in combination with the anhydride-functional polymers to prepare curable compositions in the practice of this invention should have an average of at least two primary oz, secondary amine groups per molecule. Polyamines can be prepared by methods well known in the art such as by the free radical polymerization of acrylic or other unsaturated monomers having primary or secondary amine functionality, or by the reaction of amines having at least two amine groups per molecule with a polycarboxylic acid to form polyamide amines, or by the reaction of primary amines with epoxy materials to produce secondary amine and hydroxyl functionality. The polyamines can be polymeric, typically having a number average molecular weight over 400, or lower molecular materials, such as piperazine, tetraethylenepentamine, 1,2-diaminopropane, 1,6-diaminohexane, etc. Also useful are the materials having a primary or secondary amine group and a hydroxyl group such as isopropanol amine, isobutanol amine, ethanol amine, etc.

The ratios of anhydride to other functional groups in the curable compositions can be widely varied within the practice of this invention as long as at least some of each group is present in the reactive composition it is only necessary to combine the anhydride-functional polymer and other reactive materials in amounts to provide the desired degree of crosslinking upon cure. When a combination of the anhydride-functional polymer and a polyol or polyamine is used as the curable composition, it is preferred to provide about 0.3 to about 10 hydroxyl or amine groups for each anhydride group, and especially 1 to about 5 hydroxyl or amine groups for each anhydride group. When the curable composition involves a combination of only the anhydride-functional polymer, an epoxide or polyepoxide, and a polyol it is preferred to provide 0.3 to about 6.0 hydroxyl groups, and about 0.3 to about 6.0 epoxy groups for each anhydride group, and especially to provide 0.5 to 2.5 hydroxyl groups and 0.5 to 2.5 epoxy groups for each anhydride group. When the curable composition involves the anhydride-functional polymer, an acid-functional compound and a polyepoxide, it is preferred to provide 0.3 to 6.0 acid groups and 0.6 to 12.0 epoxy groups for each anhydride group, and especially 2.0 to about 5.0 acid groups and 3.0 to about 8.0 epoxide groups for each anhydride group. If the reactive curable composition comprises the anhydride-functional polymer, an acid-functional compound, an epoxide or polyepoxide, and a hydroxy-functional compound, it is preferred to provide from 0.05 to about 3.0 acid groups and about 0.5 to about 4.0 epoxy groups and about 0.05 to 6.0 hydroxyl groups for each anhydride group in the reactive system. It is especially preferred to provide 1.0 to about 2.0 acid groups and 1.0 to about 3.0 epoxy groups and about 1.0 to about 4.0 hydroxyl groups for each anhydride group.

The curable compositions of this invention can be cured at temperatures ranging from about room temperature up to about 350° F. When the curable compositions are utilized as coatings, the coatings can be clear coatings or they may contain pigments as is well known in the art. Representative opacifying pigments include white pigments such as titanium dioxide, zinc oxide, antimony oxide, etc. and organic or inorganic chromatic pigments such as iron oxide, carbon black, phthalocyanine blue, etc. The coatings may also contain extender pigments such as calcium carbonate, clay, silica, talc, etc.

The coatings may also contain other additives such as flow agents, catalysts, diluents, solvents, ultraviolet light absorbers, etc.

It is especially preferred in the curable compositions of this invention to include a catalyst for the reaction of anhydride groups and hydroxyl groups and/or a catalyst for the reaction of epoxy and acid groups if present in the curable compositions. It is especially preferred in the practice of this invention to utilize tertiary amines and especially N-methylimidazole as a catalyst for the anhydride/hydroxyl reaction. The catalyst for the anhydride/hydroxyl reaction will typically be present at a level of at least 0.01% by weight of the anhydride compound and preferably 1.0 to about 5.0%.

Tertiary amines, secondary amines such as ethyl imidazole, quaternary ammonium salts, nucleophilic catalysts, such as lithium iodide, phosphonium salts, and phosphines such as triphenyl phosphine are especially useful as catalysts for epoxy/acid reactions. The catalyst for the epoxy/acid reaction will typically be present at a level of at least 0.01% by weight of the total acid-functional compound and epoxy-functional compound and will preferably be present at 0.1 to about 3.0%.

Since the curable compositions of this invention are typically provided as multi-package systems which must be mixed together prior to use, the pigments, catalysts and other additives can be conveniently added to any or all of the appropriate individual packages.

The curable compositions may typically be applied to any substrate such as metal, plastic, wood, glass, synthetic fibers, etc. by brushing, dipping, roll coating, flow coating, spraying or other method conventionally employed in the coating industry.

One preferred application of the curable coatings of this invention relates to their use as clearcoats and/or basecoats in clearcoat/basecoat formulations.

Clearcoat/basecoat systems are well known, especially in the automobile industry where it is especially useful to apply a pigmented basecoat, which may contain metallic pigments, to a substrate followed by the application of a clearcoat which will not mix with or have any appreciable solvent attack upon the previously applied basecoat. Typically, at least some of the solvent will be allowed to evaporate from the basecoat prior to the application of the clearcoat. In some applications the basecoat may even be allowed to cure, at least partially, prior to application of the clearcoat. The basecoat composition may be any of the polymers known to be useful in coating compositions including the reactive compositions of this invention.

One useful polymer basecoat includes the acrylic addition polymers, particularly polymers or copolymers of one or more alkyl esters of acrylic acid or methacrylic acid, optionally together with one or more other ethylenically unsaturated monomers. These polymers may be of either the thermoplastic type or the thermosetting, crosslinking type which contain hydroxyl or amine or other reactive functionality which can be crosslinked. Suitable acrylic esters for either type of polymer include methyl methacrylate, ethyl methacrylate, propyl methacrylate, butyl methacrylate, ethyl acrylate, butyl acrylate, vinyl acetate, acrylonitrile, acrylarhide, etc. Where the polymers are required to be of the crosslinking type, suitable functional monomers which can be used in addition to those already mentioned include acrylic or methacrylic acid, hydroxy ethyl acrylate, 2-hydroxy propyl methacrylate, glycidyl acrylate, tertiary-butyl amino ethyl methacrylate, etc. The basecoat composition may, in such a case, also contain a crosslinking agent such as a carbodiimide, a polyanhydride, a polyisocyanate a polyepoxide, or a nitrogen resin such as a condensate of an aldehyde such as formaldehyde with a nitrogenous compound such as urea, melamine or benzoguanamine or a lower alkyl ether of such a condensate. Other polymers useful in the basecoat composition include vinyl copolymers such as copolymers of vinyl esters of inorganic or organic acids, such as vinyl chloride, vinyl acetate, vinyl propionate, etc., which copolymers may optionally be partially hydrolyzed so as to introduce vinyl alcohol units.

Other polymers useful in the manufacture of the basecoat include alkyd resins or polyesters which can be prepared in a known mariner by the condensation of polyhydric alcohols and polycarboxylic acids, with or without the inclusion of natural drying oil fatty acids as described elsewhere in this specification. The polyesters or alkyds may contain a proportion of free hydroxyl and/or carboxyl groups which are available for reaction, if desired with suitable crosslinking agents as discussed above.

If desired, the basecoat composition may also contain waxes, theology modifiers, cellulose esters, or other additives to alter the appearance, drying or viscosity characteristics of the basecoat.

Typically, the basecoat will include pigments conventionally used for coating compositions and after being applied to a substrate, which may or may not previously have been primed, the basecoat will normally be allowed sufficient time to form a wet polymer film which will not be lifted during the application of the clearcoat. The clearcoat is then applied to the surface of the basecoat, and the system can be allowed to dry or, if desired, can be force dried by baking the coated substrate at temperatures typically ranging up to about 250° F.

Typically, the clearcoat may contain ultraviolet light absorbers or stabilizers, such as hindered phenols or hindered amines at a level ranging up to about 6% by weight of the vehicle solids as is well known in the art. The clearcoat can be applied by any application method known in the art, but preferably will be spray applied. If desired, multiple layers of basecoat and/or clearcoat can be applied. Typically, both the basecoat and the clearcoat will each be applied to give a dry film thickness of about 0.01 to about 6.0, and especially about 0.5 to about 3.0 mils.

The following examples have been selected to illustrate specific embodiments and practices of advantage to a more complete understanding of the invention. Unless otherwise stated, "parts" means parts-by-weight and "percent" is percent-by-weight.

EXAMPLE A

A reaction vessel fitted with a temperature control device, a stirring bar, a condenser, a drying tube and a heating mantle was charged with a mixture of 36 parts methacrylic anhydride, 13.4 parts DL-malic acid, and 0.05 parts concentrated sulfuric acid. The mixture was stirred at room temperature for 1 hour and then the reaction temperature was kept at 80° C. for an additional hour. The product mixture was cooled and vacuum distilled at room temperature for 10 minutes followed by vacuum distillation by a rotary evaporator at 80° C. for 10 minutes and 100° C. for an additional 10 minutes to remove excess methacrylic anhydride and by-products. The residue from the distillation was crystallized from anhydrous ether and vacuum dried overnight. The product, which was produced in approximately 92% yield, was identified by both FT infrared and NMR to be the desired (2-succinic anhydride)methacrylate (the product could alternatively be named 2-(methacryloxy)-succinic anhydride).

EXAMPLE B

A reaction vessel equipped as described in Example A was charged with a mixture of 32.8 parts methacrylic anhydride, 13.5 parts DL-malic acid and 0.05 parts concentrated sulfuric acid. The reaction mixture was heated to 80° C. from room temperature in approximately 10 minutes at which point the heating was stopped and the reaction continued to exotherm to about 85° C. The heterogeneous mixture became a clear solution at 85° C. and was allowed to cool to room temperature and 0.01 parts butylated hydroxy toluene was added to the mixture. The product mixture was vacuum distilled to remove unreacted methacrylic anhydride and by-products, and the reaction product was worked up as described in Example A. The product was identified by FT infrared to be the desired (2-succinic anhydride)methacrylate.

EXAMPLE C

A reaction vessel equipped as described in Example A was charged with a mixture of 13.4 parts DL-malic acid and 29.0 parts methacryloyl chloride. The reaction mixture was heated to 80° C. with stirring while under a nitrogen purge. Within approximately 1 hour 20 minutes the heterogeneous mixture had become a red solution which was vacuum distilled at 50° C. for 15 minutes and 100° C. for 5 minutes to yield a residue which contained primarily the desired (2-succinic anhydride)methacrylate.

EXAMPLE 1

A reaction vessel equipped with a stirring bar, a heat controller and a dropping funnel was charged with 23 parts methyl isobutyl ketone and heated to 100° C. under nitrogen purge. A solution of 9.2 parts of (2-succinic anhydride)methacrylate, 9.2 parts butyl acrylate, 4.6 parts styrene, and 1.38 parts t-butyl peroctoate was added dropwise to the heated solvent solution over 2½ hours. The temperature was raised to 110° C. approximately 40 minutes after the initiation of the reaction and the reaction was maintained at that temperature for approximately ½ hour after the monomer addition was completed. The final transparent anhydride-functional polymer had a number average molecular weight of approximately 3,500 (relative to polystyrene standard), a polydispersity of 2.0, an observed glass transition temperature of 52.1° C., a density of approximately 8.05 lbs/gallon, and a Brookfield viscosity of approximately 200 centipoise at a percent weight solids (NVM) of 52.9%.

EXAMPLE 2

A reaction vessel equipped as described in Example 1 was charged with 83 parts methyl amyl ketone and heated to 100° C. A solution of 75 parts of (2-succinic anhydride)methacrylate, 100 parts butyl acrylate, 25 parts butyl methacrylate, 25 parts styrene, 25 parts methyl methacrylate, and 20 parts t-butyl peroctoate was added dropwise to the heated solution over 2 hours. The reaction temperature was then held at 100° C. for ½ hour after completing the addition of the entire monomer mixture. An additional 2.5 parts of t-butyl peroctoate was added and the reaction mixture was maintained at 100° C. for an additional ½ hour. The final transparent anhydride-functional polymer was 71.6% NVM by the and exhibited a density of 8.51 lbs/gallon, a number average molecular weight of approximately 4,400 (relative to polystyrene standard), a polydispersity of 3.1 and an observed glass transition temperature of 31.3° C.

EXAMPLE 3

A reaction vessel equipped as described in Example 1 was charged with 167 parts Dowanol® PM acetate (propylene glycol monomethyl ether acetate commercially available from Dow Chemical Company) and heated to 115° C. A solution of 225 parts butyl acrylate, 50 parts butyl methacrylate, 150 parts (2-succinic anhydride)methacrylate, 50 parts styrene, 25 parts methacrylic acid, and 40 parts t-butyl peroctoate was added dropwise to the heated solution over a 3 hour period. The reaction temperature was then held at 115° C. for an additional ½ hour after completing the addition of the entire monomer mixture. An additional 5.0 parts of t-butyl peroctoate in 47 parts methyl amyl ketone was added to the reaction mixture and maintained at that temperature for approximately ½ hour. The final transparent anhydride-functional polymer had an NVM of 72%, a number average molecular weight of approximately 4,500 (relative to polystyrene standard), a polydispersity of 2.9, a Brookfield viscosity of 404 poise and an observed glass transition temperature of 31.6° C.

EXAMPLE 4

A clear curable composition, suitable for use as a clearcoat in clearcoat/basecoat coating applications, was prepared by admixing the anhydride-functional resin of Example 1 and Tone® 05 (polycaprolactone triol commercially available from Union Carbide Corporation having a molecular weight of about 540 and a hydroxyl equivalent weight of about 180) at a ratio to provide one anhydride group per each hydroxy group. Approximately 1% of N-methylimidazole based upon anhydride resin solids was added to the mixture as catalyst and the curable composition was applied to a steel substrate and allowed to dry at room temperature. The curable composition gave good hardness and resistance to methyl ethyl ketone.

EXAMPLE 5

A clear curable composition suitable for use as a clearcoat in a clearcoat/basecoat coating composition, was prepared by mixing at a ratio to provide one epoxy group and one hydroxy group for each anhydride group, the anhydride-functional polymer of Example 1, Tone® 305, and ERL-4229 (cycloaliphatic diepoxide commercially available from Union Carbide Corporation). The curable composition was applied to a steel substrate and allowed to dry at room temperature to give a hard cured film having good resistance to methyl ethyl ketone.

EXAMPLE 6

A curable composition was prepared by admixing the anhydride-functional polymer of Example 3, a hydroxy-functional acrylic polymer, and epoxy resin ERL-4299 in amounts to provide an equivalent ratio of anhydride groups to hydroxyl groups to epoxy groups of 2/½. The clearcoat composition was catalyzed with N-methylimidazole at 0.1% weight solids based on total reactive resin solids. The clearcoat was spray applied over Q-steel panels coated with a commercial primer, commercial sealer and a commercial basecoat and allowed to air dry at ambient room temperature. The clearcoat dried to a hard film overnight and showed good resistance to methyl ethyl ketone and good hardness.

The hydroxy-functional polymer had been prepared by initially charging a reaction vessel equipped with a mechanical stirrer, a water-cooled condenser, nitrogen inlet, thermometer, heating mantle and fluid metering pump with 1,700 parts of xylene. The xylene was heated to 135° C. and a monomer mixture composed of 970 parts styrene, 320 parts methyl methacrylate, 710 parts Tone® M100 (trademark of Union Carbides hydroxy-functional acrylic caprolactone adduct believed to be the reaction product of 1 mole of hydroxymethyl acrylate and 2 moles of caprolactone), 190 parts hydroxyethyl acrylate, 390 parts butyl acrylate and 253 parts of t-butyl peroctoate was metered into the reaction mixture over approximately 3 hours. Three individual. additions of 10.7 parts xylene and 2.6 parts t-butyl peroctoate were added to the reaction mixture at approximately 15 minutes, 30 minutes and 45 minutes after the completion of the monomer addition. The reaction temperature was then maintained at 130° C. for 2 hours. The resulting hydroxy-functional acrylic polymer had a number average molecular weight of approximately 3,000 (relative to polystyrene standard), a poly-dispersity of approximately 3.0, a Brookfield viscosity of 2.9 poise at an NVM of 59% and a density of 8.29 pounds per gallon.

Other reactive systems, such as the combination of a polyepoxy-functional material, an acid-functional material and the anhydride-functional polymer of this invention are also practical, and could, optionally, also incorporate hydroxy-functional materials as well.

While this invention has been described by a specific number of embodiments, other variations and modifications may be made without departing from the spirit and scope of the invention as set forth in the appended claims.

The entire disclosure of all applications, patents and publications cited herein are hereby incorporated by reference.

The invention claimed is:

1. In a substrate coated with a multi-layer decorative and/or protective coating which comprises:
   (a) a basecoat comprising a pigmented film-forming polymer; and
   (b) a transparent clearcoat comprising a film-forming polymer applied to the surface of the basecoat composition;
the improvement which comprises utilizing as the clearcoat and/or the basecoat a multi-component curable composition which is reactive upon mixing of the components, wherein the multi-component curable composition comprises:
   (a) an anhydride-functional polymer which comprises the polymerization which comprises the polymerization reaction product of: (i) an anhydride-functional monomer having the structure:

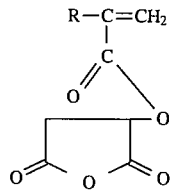

wherein R is hydrogen or methyl; and, optionally,
   (ii) at least one other unsaturated monomer copolymerizable with the anhydride-functional monomer; and
   (b) a hydroxy-functional compound having an average of at least two hydroxyl groups per molecule.

2. The coated substrate of claim 1 wherein the anhydride-functional polymer comprises the free radical polymerization reaction product of a monomer mixture comprising 5 to 100% by weight of the anhydride-functional monomer and 0 to 95 % by weight of at least one other unsaturated monomer copolymerizable with the anhydride-functional monomer.

3. The coated substrate of claim 1 wherein the anhydride-functional polymer is characterized in that R is methyl.

4. The coated substrate of claim 1 wherein the anhydride-functional polymer is characterized in that R is hydrogen.

5. The coated substrate of claim 1 wherein the anhydride-functional polymer comprises the free-radical addition polymerization product of: (i) 5 to 60 weight percent of the anhydride-functional monomer; and (ii) 40 to 95 weight percent of at least one other unsaturated monomer copolymerizable with the anhydride-functional monomer.

6. The coated substrate of claim 1 wherein the anhydride-functional polymer comprises the free-radical addition polymerization reaction product of: (i) 15 to 40 weight percent of the anhydride-functional monomer; and (ii) 60 to 85 weight percent of at least one other unsaturated monomer copolymerizable with the anhydride-functional monomer.

7. The coated substrate of claim 1 wherein the compound having an average of at least two functional groups per molecule reactive with anhydride is a polyamine.

8. The coated substrate of claim 1 wherein the compound having an average of at least two functional groups per molecule reactive with anhydride is a hydroxy-functional compound.

9. The coated substrate of claim 8 wherein the anhydride-functional polymer and the hydroxy-functional compound are each present at a level to provide 0.3 to about 10 hydroxyl groups for each anhydride group.

10. The coated substrate of claim 8 wherein the hydroxy-functional compound is a hydroxy-functional polymer.

11. The coated substrate of claim 10 wherein the hydroxy-functional polymer comprises the addition polymerization reaction product of:
   (a) 10 to about 60 weight percent of a hydroxy-functional ethylenically unsaturated monomer; and
   (b) 40 to about 90 weight percent of at least one ethylenically unsaturated monomer copolymerizable with the hydroxy-functional monomer.

12. The coated substrate of claim 8 wherein the curable composition also comprises a catalyst for reaction of hydroxy groups and anhydride groups.

13. The coated substrate of claim 8 wherein the curable composition also comprises an epoxy-functional compound having an average of at least one epoxy group per molecule.

14. The coated substrate of claim 13 wherein the anhydride-functional polyether, the hydroxy-functional compound, and the epoxy-functional compound are each present in the curable composition at a level to provide 0.3 to about 6.0 hydroxyl groups, and about 0.3 to about 6.0 epoxy groups for each anhydride group.

15. The coated substrate of claim 13 wherein the epoxy-functional compound monoepoxide.

16. The coated substrate of claim 13 wherein the epoxy-functional compound is polyepoxide having an average of at least two epoxy groups per molecule.

17. The coated substrate of claim 16 wherein the polyepoxide is a cycloaliphatic polyepoxide.

18. The coated substrate of claim 16 wherein the polyepoxide is a copolymer obtained by the copolymerization of an ethylenically unsaturated epoxy-functional monomer and at least one other copolymerizable ethylenically unsaturated monomer.

19. The coated substrate of claim 13 wherein the curable composition also comprises an acid-functional compound having an average of at least two carboxylic acid groups per molecule.

20. The coated substrate of claim 19 wherein the curable composition also comprises a catalyst for the reaction of hydroxy groups and anhydride groups and a catalyst for the reaction of epoxy groups and acid groups.

21. The coated substrate of claim 19 wherein the acid-functional compound is an acid-functional polymer.

22. The coated substrate of claim 21 wherein the acid-functional polymer is prepared by the half-ester opening of a cyclic anhydride by reaction with a hydroxy-functional polymer.

23. The coated substrate of claim 22 wherein the hydroxy-functional polymer is the addition polymerization reaction product of:
   (a) 5 to 100 weight percent of a hydroxy-functional ethylenically unsaturated monomer; and
   (b) 0 to 95 weight percent of at least one other ethylenically unsaturated monomer copolymerizable with the hydroxy-functional monomer.

24. The coated substrate of claim 19 wherein the anhydride-functional polymer, the hydroxy-functional compound, the acid-functional compound and the epoxy-functional compound are each present in the curable composition at a level to provide 0.05 to about 3.0 acid groups and about 0.5 to about 4.0 epoxy groups and about 0.05 to about 6.0 hydroxyl groups for each anhydride group.

25. In a substrate coated with a multi-layer decorative and/or protective coating which comprises:
   (a) a basecoat comprising a pigmented film-forming polymer; and
   (b) a transparent clearcoat comprising a film-forming polymer applied to the surface of the basecoat composition; the improvement which comprises utilizing as the clearcoat and/or the basecoat a multi-component curable composition which is reactive upon mixing of the components, wherein the multi-component curable composition comprises:
   (a) an anhydride-functional polymer which comprises the polymerization reaction product of: (i) an anhydride-functional monomer having the structure:

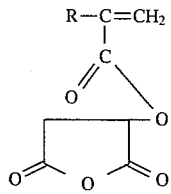

wherein R is hydrogen or methyl; and, optionally,
   (ii) at least one other unsaturated monomer copoylmerizable with the anhydride-functional monomer; and
   (b) an acid-functional compound having an average of at least two carboxylic acid groups per moleculd; and
   (c) an epoxy-functional compound.

26. The coated substrate of claim 25 wherein the anhydride-functional polymer comprises the free radical addition polymerization product of a monomer mixture comprising 5 to 100% by weight of the anhydride-functional monomer and 0 to 95% by weight of at least one other unsaturated monomer copolymerizable with the anhydride-functional monomer.

27. The coated substrate of claim 25 wherein the anhydride-functional polymer comprises the free radical additional polymerization reaction product of: (i) 5 to 60 weight percent of the anhydride-functional monomer; and (ii) 40 to 95 weight percent of at least one other unsaturated monomer copolymerizable with the anhydride-functional monomer.

28. The coated substrate of claim 25 wherein the anhydride-functional polymer comprises the free radical additional polymerizable product of: (i) 15 to 40 weight percent of the anhydride-functional monomer; and (ii) 60 to 85 weight percent of at least one other unsaturated monomer copolymerizable with the anhydride-functional monomer.

29. The coated substrate of claim 25 wherein the acid-functional compound is an acid-functional polymer.

30. The coated substrate of claim 29 wherein the acid-functional polymer is prepared by the half-ester opening of a cyclic anhydride by reaction with a hydroxy-functional polymer.

31. The coated substrate of claim 30 wherein the hydroxy-functional polymer is the addition polymerization reaction product of
   (a) 5 to 100 weight percent of a hydroxy-functional ethylenically unsaturated monomer; and
   (b) 0 to 95 weight percent of at least one other ethylenically unsaturated monomer copolymerizable with the hydroxy-functional monomer.

32. The coated substrate of claim 25 wherein the epoxy-functional compound is a monoepoxide.

33. The coated substrate of claim 25 wherein the epoxy-functional compound is a polyepoxide having an average of at least 2 epoxy groups per molecule.

34. The coated substrate of claim 33 wherein the polyepoxide is a cycloaliphatic polyepoxide.

35. The coated substrate of claim 33 wherein the polyepoxide is a copolymer obtained by the copolymerization of an ethylenically unsaturated epoxy-functional monomer and at least one other copolymerizable ethylenically unsaturated monomer.

36. The coated substrate of claim 25 wherein the anhydride-functional polymer and the acid-functional compound and the epoxy-functional compound are each present in the curable composition at a level to provide 0.3 to about 6.0 acid groups and 0.6 to 12.0 epoxy groups for each anhydride group.

37. The coated substrate of claim 25 wherein the composition also comprises a catalyst for the reaction of acid groups and epoxy groups and a catalyst for the reaction of anhydride groups and hydroxyl groups.

* * * * *